(12) United States Patent
Strannemalm (10) Patent No.: US 8,029,490 B2
(45) Date of Patent: Oct. 4, 2011

(54) ABSORBENT ARTICLE FOR USE WITH AN APPLICATION AID

(75) Inventor: Kenneth Strannemalm, Floda (SE)

(73) Assignee: SCA Hygiene Products AB, Gothenburg (SE)

( * ) Notice: Subject to any disclaimer, the term of this patent is extended or adjusted under 35 U.S.C. 154(b) by 87 days.

(21) Appl. No.: 11/747,898

(22) Filed: May 12, 2007

(65) Prior Publication Data

US 2007/0213680 A1 Sep. 13, 2007

Related U.S. Application Data

(62) Division of application No. 11/013,356, filed on Dec. 17, 2004.

(60) Provisional application No. 60/530,668, filed on Feb. 19, 2003.

(51) Int. Cl.
*A61F 13/15* (2006.01)

(52) U.S. Cl. .......... 604/392; 604/385.19; 604/398

(58) Field of Classification Search ......... 604/385.19, 604/385.201, 392, 398–399
See application file for complete search history.

(56) References Cited

U.S. PATENT DOCUMENTS

| | | | | |
|---|---|---|---|---|
| 2,058,509 A | * | 10/1936 | Rose | 604/392 |
| 2,654,367 A | | 10/1953 | Turnham | |
| 3,023,752 A | | 3/1962 | Winn | |
| 4,505,707 A | * | 3/1985 | Feeney | 604/393 |
| 4,728,326 A | * | 3/1988 | Gilles | 604/391 |
| 4,878,879 A | | 11/1989 | Kunstadter | |
| 4,917,693 A | * | 4/1990 | Terry | 604/385.06 |
| 4,937,887 A | * | 7/1990 | Schreiner | 2/402 |
| 5,722,127 A | * | 3/1998 | Coates | 24/304 |
| 5,930,875 A | * | 8/1999 | Schreiner | 24/442 |
| 7,156,834 B2 | | 1/2007 | Kawata et al. | |
| 2001/0041879 A1 | * | 11/2001 | Karami et al. | 604/386 |
| 2005/0205619 A1 | | 9/2005 | Morel | |

FOREIGN PATENT DOCUMENTS

| | | |
|---|---|---|
| GB | 2 288 125 | 10/1995 |
| WO | 02/22065 | 3/2002 |
| WO | 03/017903 | 3/2003 |

OTHER PUBLICATIONS

International Search Report and Written Opinion dated Mar. 16, 2005.

* cited by examiner

*Primary Examiner* — Lynne Anderson (74) *Attorney, Agent, or Firm* — Buchanan Ingersoll & Rooney PC (57) ABSTRACT

An absorbent article having at least one belt part with a first end secured to the absorbent article, and a second end, wherein the belt part has a feature for cooperating with an application aid so that the belt and the application aid cooperate when guided under the user.

20 Claims, 7 Drawing Sheets

ABSORBENT ARTICLE FOR USE WITH AN APPLICATION AID

CROSS-REFERENCE TO RELATED APPLICATION

The present application is a divisional of application Ser. No. 11/013,356, which claims the benefit of U.S. Provisional Application Ser. No. 60/530,668, filed on Dec. 19, 2003, the entire contents of which is hereby incorporated herein by reference.

TECHNICAL FIELD

The present invention relates to an absorbent article adapted for use with an application aid.

BACKGROUND

Each year, considerable resources are invested in developing absorbent articles such as diapers, pant diapers, belt diapers, panty-liners and tampons. The products are adapted to young children and incontinent adults so that they are as comfortable as possible and secure against leaking.

A number of inventions, such as leakage barriers on diapers, have helped give some of these individuals a more tolerable existence. The leakage barriers provide extra protection against leakage of urine and excrement via the leg openings, which can happen when the user is walking, turns in bed, or performs some other manoeuvre which can make the diaper change position.

Other inventions such as breathable materials are developed to minimize the moisture content of absorbent articles. Minimized moisture content of an absorbent article means that the skin is drier because moisture in the article dries out more quickly. Dry skin is less likely to be damaged by external action such as chafing or growth of bacterial flora.

A number of elastic threads in the waist region of diaper pants constitutes another invention which gives a better fit and improved comfort for the user. The transverse elastic threads hold the diaper in the right place during use and prevent the diaper from sliding out of position.

However, corresponding resources are not invested on those individuals who are expected to change the absorbent articles on the users. For example, caretakers such as nurses, assistant nurses and the like, whose daily work involves dealing with incontinent individuals, have a very difficult job. In the text below, "users" refers to the individuals on whom the absorbent articles are applied. Those commonly using absorbent articles include, for example, children, incontinent individuals, or menstruating women. "Caretakers" means the persons who apply the absorbent articles on the users.

Each day, the caretakers may have to move several users in order to change the absorbent article on them. They sometimes have to roll a user into the right position before the absorbent article can be applied. The problems of moving a heavy weight are sometimes exacerbated even further when, for example, the caretaker is a woman of short build and she is expected to move a large man. The caretakers often perform tasks which place a heavy strain on their backs and arms. In the long term, the heavy strain can cause injuries to the back, shoulders and joints. Moving heavy weights, in combination with a stressful working environment, means that caretakers may also experience psychological frustration at not being able to cope.

Absorbent articles with belts, so-called belt diapers, are one way of providing caretakers and users with advantageously configured products. Belt diapers are described in detail in WO 03/017903 and WO 02/22065. Despite the fact that the belt diapers have given caretakers an alternative to the customary incontinence diapers, the belt diaper is far from satisfactory. The caretaker still has to roll the patients over in order to be able to place the belt diaper under the patient's body. Such a manoeuvre often results in the caretaker having to stand leaning forward over the patient. This position, with the caretaker leaning forward, often places a weight on the back muscles, which can be tiring and can even strain the muscles.

OBJECTS AND SUMMARY

It is therefore desirable to have a method and an absorbent article which reduce the number of work steps involved in changing the absorbent article. It is also desirable to have a method which minimizes the number of wrongly performed tasks when applying the absorbent article. It is also desirable to have an absorbent article which permits the caretaker flexible solutions when changing the diaper. It is preferably desirable to have a belt diaper which permits the caretaker flexible solutions when changing the diaper. Flexible solutions make things easier because the caretaker is able to vary his/her work position in order to avoid static loading and poor work positions.

The present invention has made available a method of the type mentioned in the introduction, which method substantially avoids or alleviates the aforementioned problems. The present invention also includes a related article and an application aid.

An embodiment of the invention for applying an absorbent article on a user in a recumbent position comprises a number of steps which will be described in detail below. Put simply, an application aid is attached to the absorbent article in such a way that it cooperates with that part of the absorbent article which is to be guided under the user, and in such a way that a part of the absorbent article and the application aid are guided under the user.

The method concerned has a number of advantages compared to previously known methods for application of belt diapers. The method according to the invention reduces the number of stressed movements of a caretaker who is to change the diaper on a patient. This means that the work situation is improved and, consequently, the number of days off sick can probably also be reduced.

The method further involves the application aid being removed from the absorbent article so that the cooperation between the application aid and the absorbent article ceases. The absorbent article can then be joined together so that it surrounds the user.

The application aid can preferably be arranged so that it cooperates with the belt, and preferably with a fastening device arranged on the belt, for example a pocket-like receiving part. This means that the application aid does not lose contact with the belt part when it is pushed in under the patient. Nor does the application aid chafe the patient's skin or catch in the bedclothes or the patient's clothes when the application aid lies enclosed in the receiving part.

The application aid may have a fastening device for cooperating with the absorbent article and preferably the belt on the absorbent article. In one embodiment of the invention, both the application aid and the absorbent article can have fastening devices so that the absorbent article and the application aid cooperate upon movement of the absorbent article or the application aid.

An embodiment of the invention also comprises an absorbent article which can be used in conjunction with the method or independently. The absorbent article expediently comprises a substantially liquid-impermeable backing material, a liquid-permeable cover sheet, and enclosed between these an absorption body. Moreover, the article has a front portion, a rear portion, and a crotch portion placed between these, and also two longitudinal sides and two transverse sides. The article also has at least one belt part. The belt part has a first end secured to the absorbent article, and a second end. The belt part also has means for arranging an application aid so that the belt and the application aid cooperate upon movement of the absorbent article or the application aid.

In one embodiment, the absorbent article has a first belt part and a second belt part. In such an embodiment, at least one of the first and second belt parts has means for arranging an application aid. The means can, for example, consist of a pocket-like receiving part for insertion of the application aid.

It can be economically advantageous to have only one receiving part such as a pocket-like receiving part on the belt. However, to ensure a caretaker's flexibility and well-being, it can be advantageous to have a receiving part on both the first belt part and the second belt part. This makes things easier for the caretaker and saves time.

From the production point of view, the pocket-like receiving part can thus be formed by the belt part. The receiving part can be produced in-line or separately and then attached to the absorbent article as ready-made belt parts. In one embodiment, the belt parts can at least partially consist of the same layers of material as the rear portion of the absorbent article.

The second end of the belt part is preferably folded over the belt part towards the first end of the belt part so that the longitudinal sides of the belt part run substantially parallel to one another. The sides of the pocket can be welded by ultrasound or glued or otherwise joined so that the pocket-like receiving part is formed. The join which creates the pocket-like receiving part does not need to be permanent and instead can consist of a temporary attachment which after use can be unfolded so that the belt returns to its full length. However, it can be advantageous for the pocket-like receiving part to comprise a material separate from the belt part, for example a fastening device such as a hook or loop material. Other fastening devices can also be used depending on what material the belt is to be fastened to.

An embodiment of the invention also concerns an application aid which is expediently made of a flexible material, for example a plastic material, metal material or wood material. The flexibility of the application aid makes it easy to guide under the user's body without catching on or chafing the user. However, it is also possible to have a non-flexible material, but this is not so advantageous because it is more difficult to make a non-flexible material follow the shape of a user's body during application.

The application aid can be designed with a rectangular shape, for example similar to a batten, a ruler, or an arrangement like a shoehorn. Suitable dimensions are 15-100 cm in length and 2-14 cm in width. The thickness can be adapted to the material used. It is expedient for the invention that a flexible arrangement is obtained. However, too much flexibility is not desirable because this can lead to difficulties in guiding the application aid under the patient.

An advantageous embodiment of the application aid is where it comprises a fastening device to which the belt can be secured. The fastening device consists preferably of a hook or loop material, a clip arrangement, press-studs or the like. Hook material can be used when the belt material consists of a nonwoven laminate which can itself be used as loop material. Loop material on the application aid could be used when the belt part has a hook surface. In one embodiment, the fastening device of the application aid has both hook material and loop material. The advantage of such an embodiment is that the belt part itself does not need to be modified. In this way the number of process steps can be reduced, as can the costs of producing the diaper. The production costs can instead be shifted to the application aid. This also gives a caretaker a tool which can be used with products already on the market.

BRIEF DESCRIPTION OF THE FIGURES

The invention will be described in greater detail below with reference to the figures shown on the attached drawings, where.

DETAILED DESCRIPTION OF THE PREFERRED EMBODIMENTS

Figure 1:
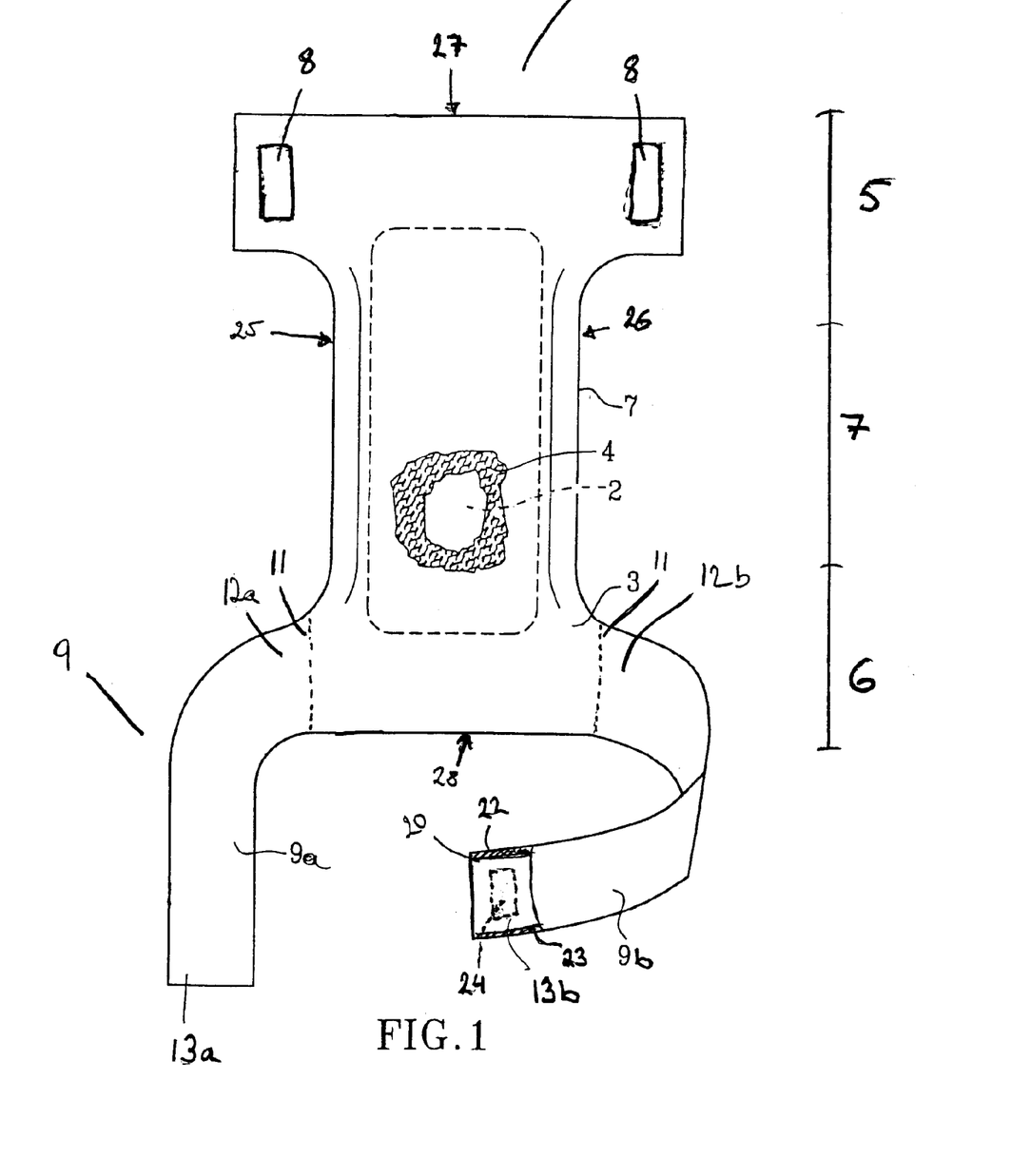
FIG. 1 shows an embodiment of a belt diaper in a view looking towards the liquid-permeable cover sheet.

FIG. 1 shows an illustrative embodiment of an absorbent article in the form of a belt diaper 1 comprising a substantially liquid-impermeable backing material 2, a liquid-permeable cover sheet 3, and an absorption body 4 enclosed between these. The liquid-permeable cover sheet 3 can comprise nonwoven material, for example spunbond material of continuous filaments, meltblown material, bonded carded fibre material, perforated plastic film, or combinations of these. The liquid-impermeable backing material 2 can include material such as a plastic film, nonwoven material which has been coated with a liquid-blocking material or hydrophobic nonwoven material which resists liquid penetration. The backing material 2 is preferably breathable. A breathable material means a material which can let water vapour pass through. Examples of such materials are well known in the field and are not described in detail here.

The backing material 2 and the cover sheet 3 have a slightly greater planar extent than the absorption body 4 and extend beyond the edges of the latter. The sheets 2 and 3 are connected to one another inside the protruding portions, for example by gluing or welding with heat or ultrasound.

The absorption body 4 can be of any conventional type. Examples of conventional absorption materials are cellulose fluff pulp, tissue layers, superabsorbent polymers (called superabsorbents or SAPs), absorbent foam material, absorbent nonwoven material and the like. It is customary to combine cellulose fluff pulp with superabsorbents in an absorption body. It is also customary to have absorption bodies built up from sheets of different materials with different properties as regards liquid uptake, spreading capacity and storing capacity. This is known to the skilled person in this field and therefore does not need to be described here. The thin absorption cores which are customary in, for example, baby diapers and incontinence guards often consist of a compressed mixed or layered structure of cellulose fluff pulp and superabsorbents.

The belt diaper is intended to enclose the lower part of the user's trunk like a pair of absorbent briefs. It has a front portion 5 intended to be directed forwards on the user during use, a rear portion 6 intended to be directed rearwards on the user during use. Arranged between the front portion and rear portion there is a narrower crotch portion 7 which is intended to be arranged at the user's crotch between his/her legs. The front portion 5 has a pair of front fastening devices 8 of the hook and loop type. Adhesive fastening means can also be used.

First and second belt parts 9a, 9b have first ends 12a, 12b secured, for example glued or welded by ultrasound along a line 11, to the rear portion 6 of the diaper. According to a second embodiment, the belt parts can consist of the same sheets as the rear portion 6. The second ends 13a, 13b of the first and second belt parts 9a, 9b are intended to be fastened together with a belt-fastening device 24. The belt-fastening device 24 can consist of hook and loop material, for example Velcro®, or of an adhesive fastening means. The front fastening devices 8 of the front portion 5 are intended to be fastened to the outsides of the belt parts 9a, 9b in order to fasten the belt diaper together to give the desired briefs shape.

According to an alternative embodiment (not shown), the first and second belt parts 9a, 9b are fastened to the front portion 5 of the diapers and are thus intended to be joined together across the wearer's back. The fastening devices 8 are then arranged on the rear portion 6 of the diaper as a rear fastening device.

Figure 2A:
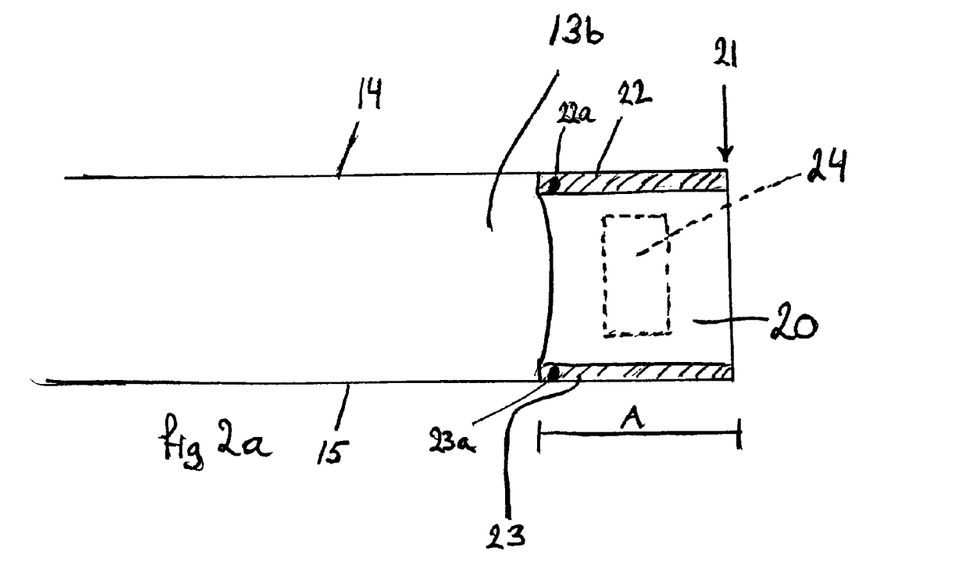
FIG. 2A-2B shows one end of a belt part and the pocket-like receiving part.

In order to provide a comfortable fit, the width of the belt parts 9a, 9b should be between 5 and 20 cm, preferably between 7 and 15 cm. The belt parts 9a, 9b expediently consist of a laminate of a carrier material, which forms the outside of the belt, and a soft nonwoven which forms the inside of the belt, intended to bear directly on the user's skin. A suitable nonwoven material can consist of a spunbond material, for example of polypropylene or polyethylene fibres. Bi-component fibres can also be used. Another suitable nonwoven material consists of a carded heat-bonded material, for example polypropylene, polyester or bi-component fibres. As carrier material it is possible to use a plastic film or other suitable material, for example the aforementioned nonwoven materials. The carrier material can be adapted to function as a receiving surface for the front fastening devices 8. In the case where these consist of adhesive tapes, a plastic film is suitable. In the case where other types of fastening devices are used instead of adhesive tapes, for example hook and loop materials, another type of carrier material is needed which can function as a receiving surface for the fastening device in question. Elastic laminates are also suitable for use as material in the belt parts 9a, 9b. An important detail is that the belt parts 9a, 9b are preferably breathable so as not to occlude the skin of the user wearing them. FIG. 2a shows the second end 13b of the second belt part 9b in the extended state. The second end 13b of the second belt part 9b has a receiving part 20 for temporary attachment of a fastening aid 50.

The receiving part 20 can be designed in a number of different ways. The pocket-like receiving part shown in FIG. 2a will be described first. The pocket-like receiving part 20 is formed by the second end 13b of the second belt part 9b having been folded a distance A along a line 21 over the second belt part 9b towards the first end 12b of the second belt part 9b, so that the longitudinal sides 14, 15 of the second belt part 9b run substantially parallel to one another.

The sides of the pocket-like receiving part 20 are connected by connections 22, 23 to the second belt part 9b so that a pocket is formed for insertion of the application aid 50. The connections 22, 23 are formed by glue, ultrasound or any other connection technique known in this field. The distance A must be sufficiently long for part of the application aid to be inserted into the pocket temporarily without risk of its falling out upon application of the absorbent article. In one embodiment of the invention, the pocket-like receiving part is big enough for a fully grown man's hand to be inserted into the pocket. It has been found that suitable measurements for the distance A are ca. 2-20 cm, preferably 4-10 cm.

In another embodiment, the connections 22, 23 can consist of two individual bonds 22a, 23a, or a plurality of bonds which run in successive rows (not shown). The important point is that a pocket-like receiving part is obtained.

In another embodiment within the scope of the invention, the pocket-like receiving part 20 can be produced separately and then be secured in-line to a belt part 9. It can alternatively be secured on a belt part 9 before said belt part 9 is secured to the backing material 2. It is possible within the scope of the invention that the first belt part 9a has a pocket-like receiving part. Alternatively, both the first and the second belt parts 9a, 9b can have pocket-like receiving parts. The invention is of course also applicable to diaper pants which have only one belt part.

The second end 13 of the belt part 9 can also have fastening devices 24 to which corresponding belt parts 9 are to be attached.

Figure 2B:
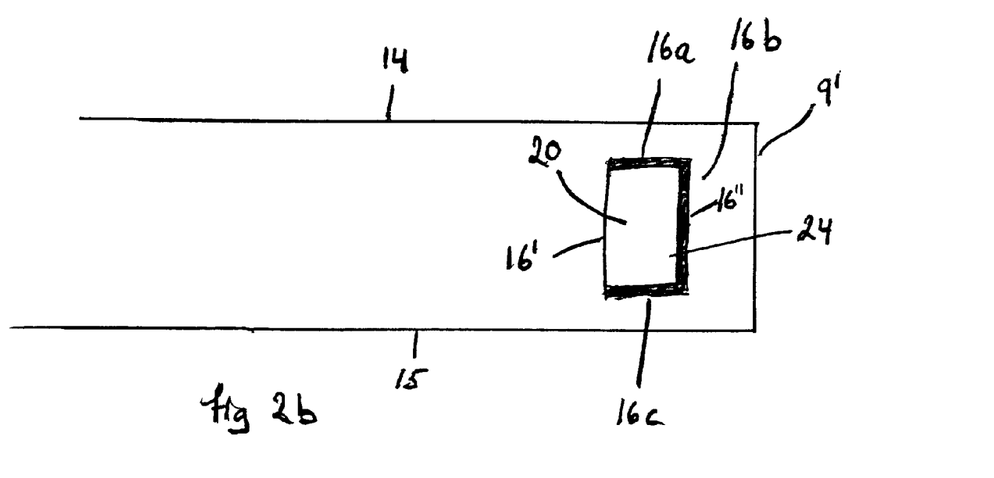

FIG. 2b shows an embodiment of the invention in which the pocket-like receiving part consists of the fastening device 24 which is preferably made of a hook or loop material. In FIG. 2b, the fastening device 24 is of rectangular shape, placed so that its longitudinal sides 16', 16" run substantially parallel to the transverse edge 9' of the belt part 9. The fastening device 24 is secured to the belt part 9 so that a pocket-like receiving part 20 is obtained. In FIG. 2b, this is done by only three of the four sides of the fastening device being secured to the belt part 9. The attachment points in FIG. 2b are indicated as 16a, 16b and 16c.

Figure 3:
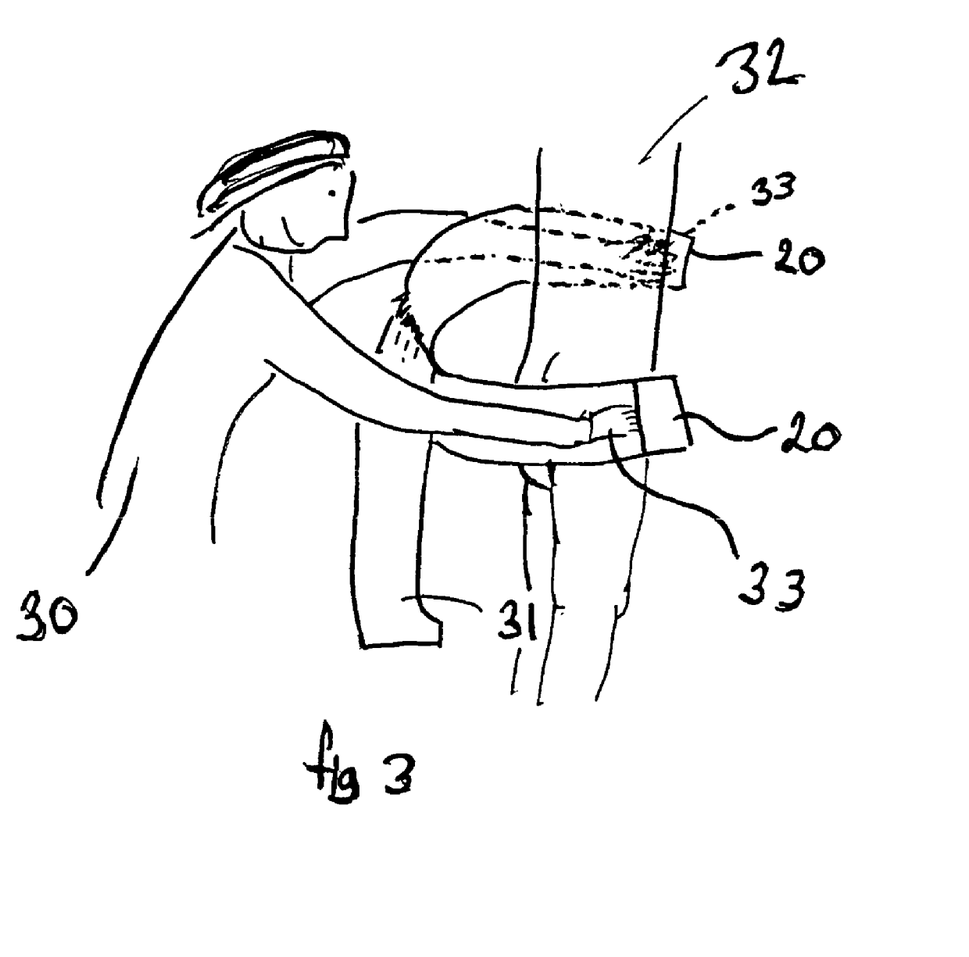
FIGS. 3-5 show a caretaker using an embodiment of the invention to change a diaper on a patient.

FIG. 3 shows how a caretaker 30 secures an incontinence diaper 1 onto a user 32 who is standing. The caretaker 30 has inserted his/her hands into the pocket-like receiving part 20 and can easily and simply secure the diaper 1 by reaching round the user 32 from the rear and bringing the belt parts 9 together.

Figure 4:
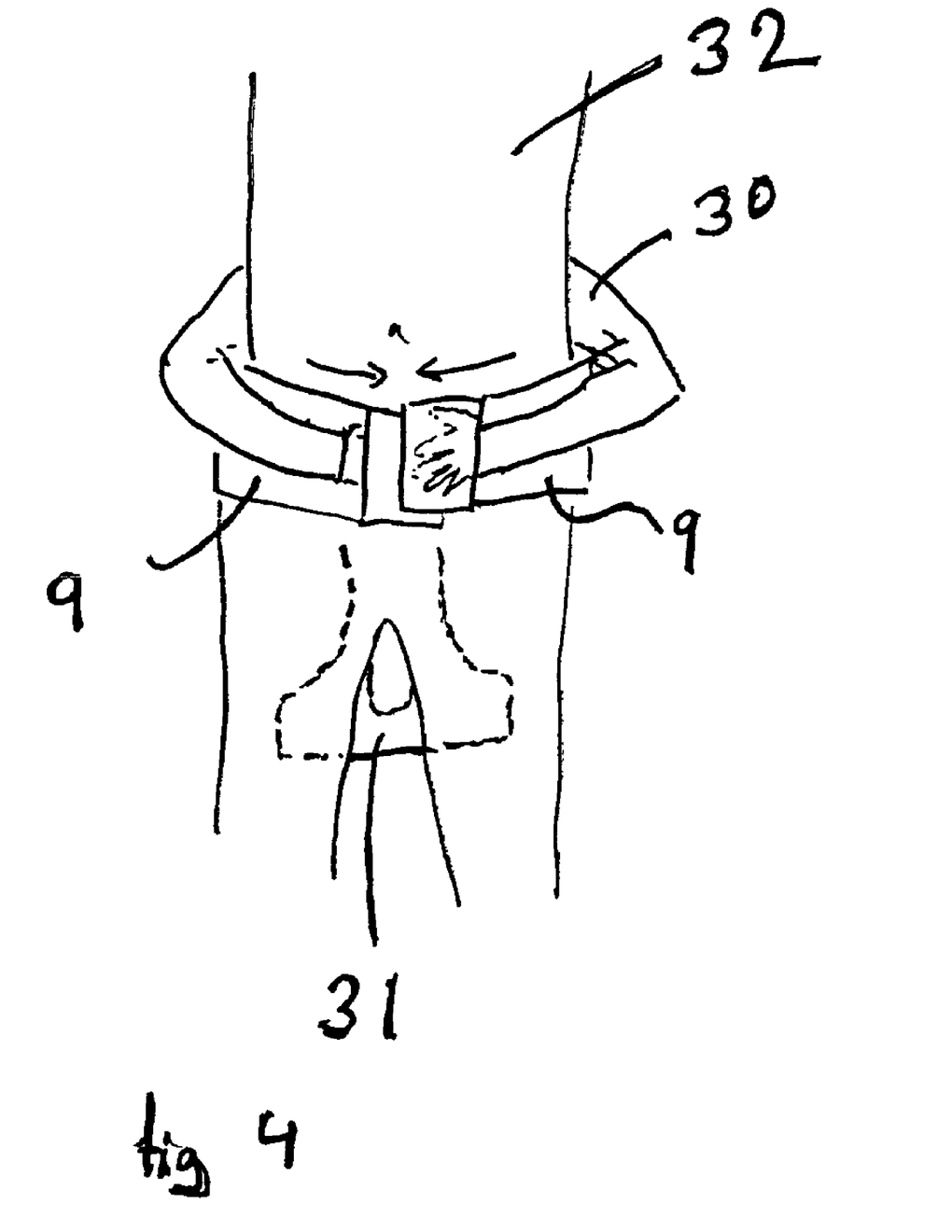

FIG. 4 shows how the caretaker 30 reaches round the user 32 from the rear and can in this way easily and simply fasten the belt parts 9 of the diaper. A further advantage of the invention is that the caretaker can feel with his/her own hands that the belt is really fastened.

Figure 5:
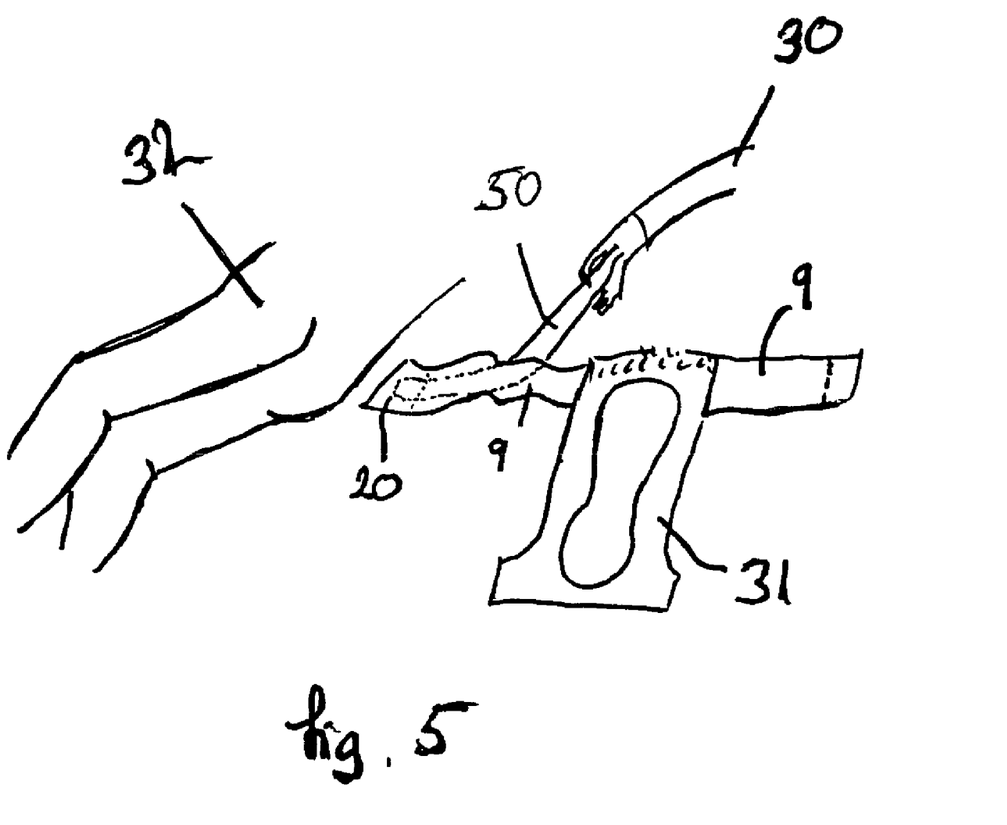

FIG. 5 shows another method of fastening a belt diaper. The caretaker 30 here uses a fastening aid 50 in the form of a thin, flexible and flat application aid which makes it easy for the caretaker 30 to guide one end of the belt 9 under the user's body and fasten the belt parts 9 and the diaper 1, without having to adopt an ergonomically disadvantageous position. A further advantage is that the caretaker 30 does not have to lift or roll the user 23 to get the belt part 9 under the user 32.

The diaper 1 is fastened on a recumbent user by attaching the application aid 50 to the receiving part 20 so that it cooperates with the belt part. The application aid can for example be inserted into a pocket-like receiving part on the belt part 9, as has been described earlier. Alternatively, the application aid can be secured on the belt directly with a fastening device such as a hook material, a clip or similar. The application aid 50 and the belt part 9 are then guided from one side of the user under the user's waist, back or stomach so that they stick out and can be easily reached from the user's other side. The second belt part 9b can then be laid across the user 32 so that the belt parts 9 enclose the user 32. Thereafter, the belt parts 9 are secured to one another by the respective fastening device. The front part 5 of the diaper 1 is then folded up between the user's legs and secured to the belt parts 9 so that the diaper 1 is given a briefs shape.

The application aid 50 can consist of a flat arrangement not entirely unlike a batten, a ruler or a shoehorn. An arrangement with a circular cross section can also be used. The length is preferably 15-100 cm long and 2-14 cm wide in the case of a flat arrangement. The thickness of the flat arrangement varies so that suitable flexibility is achieved for the chosen material. Suitable measurements for the thickness can be 1-5 mm when using a plastic material, but even thinner when using steel material, for example 0.3-3 mm. A thin, flat fastening aid makes it easy to guide the belt under the user when fastening the diaper, without the application aid catching on clothes, the user or other bedclothes. The application aid 50 is also advantageously designed with a handpiece so that the caretaker can grip it in an ergonomic manner. It is also advantageously made of a material which slides with as little as possible friction against the skin and bedclothes. When the application aid comprises an arrangement of circular cross section, the length is preferably 15-100 cm and the diameter 0.3-1.5 cm. Here too, the application aid is preferably made of a flexible material.

The application aid can be made of a plastic material, for example cellulose plastic, such as cellulose acetate, cellulose acetate butyrate, cellulose acetate propionate, or of other plastics such as polystyrene, polyacrylates, e.g. polymethacrylate, polyethylene, polypropylene, polyamide, polyvinyl chloride (PVC). The application aid can be made of a transparent material or of colored material.

Figure 6A:
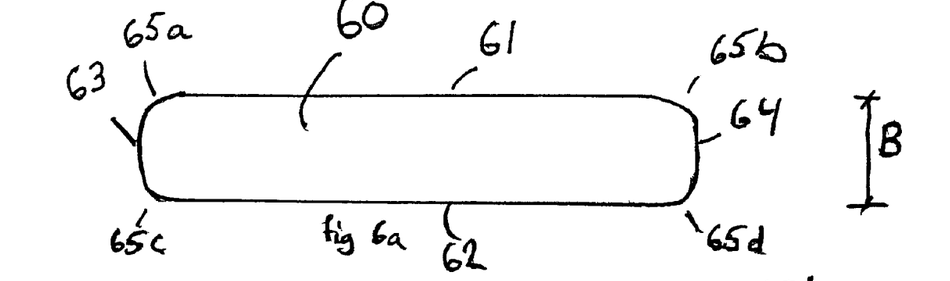
FIG. 6A-6D and 7A-7B show different embodiments of the application aid.
Figure 6B:
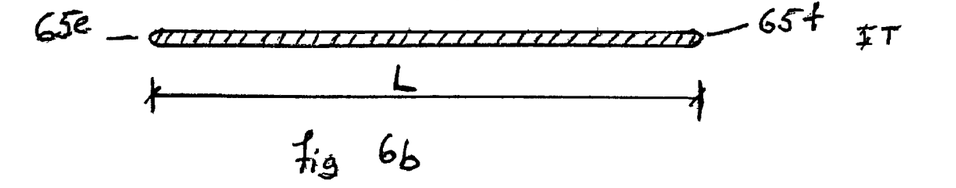
Figure 6C:
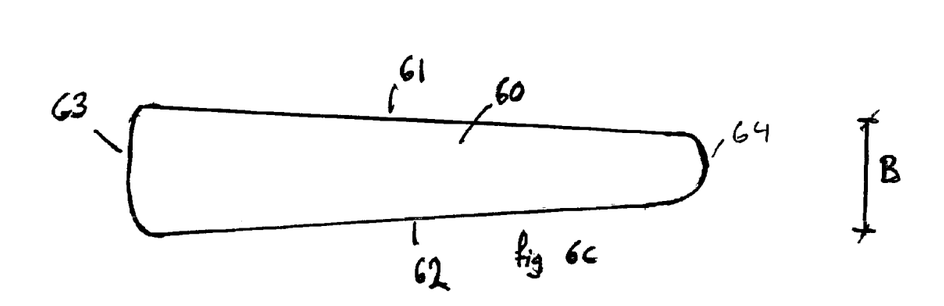
Figure 6D:
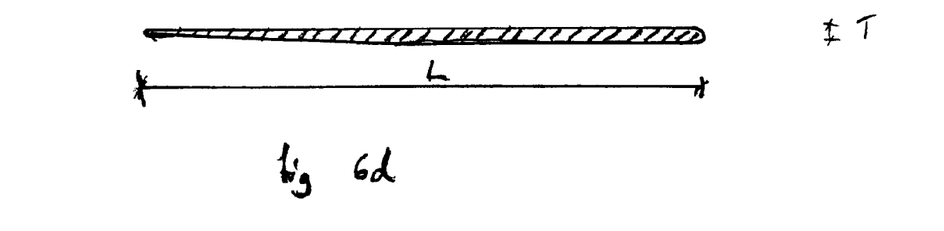
Figures 7A, 7B:
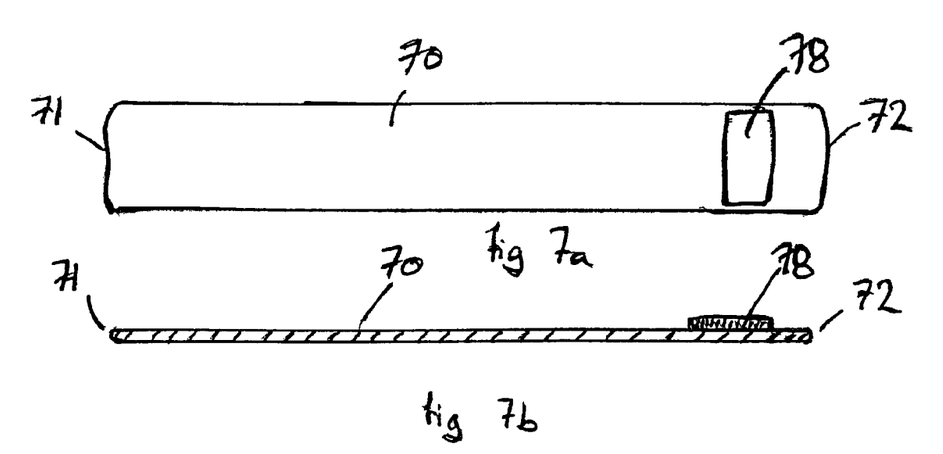

FIGS. 6-7 show several embodiments of the application aid.

FIG. 6*a* shows a simple embodiment of a flexible batten-shaped or ruler-shaped application aid 60 with a length L. In the illustrative embodiment shown, the length L is ca. 50 cm, but in other embodiments it can vary from ca. 15 to 100 cm. The width B is ca. 3.5 cm, but it too can vary within the scope of the invention. The thickness T is 3 mm, but this can also vary in other embodiments. The application aid 60 in FIG. 6*a* is made of transparent polystyrene.

The application aid in FIG. 6*a* has a substantially rectangular shape with two longitudinal sides 61, 62 and two transverse sides 63, 64. It also has rounded corners 65*a*, 65*b*, 65*c*, 65*d* so as not to scratch the user when the belt is guided under the user. FIG. 6*b* shows a cross section through the application aid 60 in the longitudinal direction. In FIG. 6*b*, the application aid 60 also has a rounding of the transverse edges 63, 64 in the direction of thickness in order to further simplify the insertion under the patient. The application aid in FIGS. 6*a*-6*b* is completely symmetrical in shape. This means that it is easy and inexpensive to produce. In other embodiments, the shapes may vary. FIGS. 6*c*-6*d* show an asymmetrical application aid 60. The two longitudinal sides 61, 62 narrow slightly so that the width B decreases in the direction from one transverse edge 63 towards the other transverse edge 64. The width at one transverse edge 63 is ca. 4.5 cm in this embodiment, while the second transverse side 64 has a width of ca. 2.5 cm. FIG. 6*d* shows a cross section of the application aid 60 in the longitudinal direction. The thickness T also varies in the longitudinal direction, as is seen in FIG. 6*d*. At one transverse side 63, the thickness is ca. 2.5 mm, while the thickness T is ca. 4.5 mm at the other transverse side 64. By varying the thickness and the width in the longitudinal direction, the application aid is given a varying degree of stiffness.

FIG. 7*a* shows an application aid 70 with two transverse sides 71, 72 and with a fastening device 78 placed near one transverse side 72. In this illustrative embodiment, the fastening device 78 can be glued into place.

FIG. 7*b* shows an application aid 70 of substantially rectangular shape in a cross section in the longitudinal direction. In FIGS. 7*a*-7*b*, the fastening device 78 consists of a hook material for fastening on the belt part 9, which will then function as a loop material for the application aid 70. Alternatively, the belt part 9 can have a separate loop material for the application aid 70. In another embodiment not shown, the fastening device 78 is designed as a clip, a glued surface or similar arrangement secured to the belt part 9. The advantage of an application aid of this kind is that the belt part 9 does not have to have a specific receiving part and instead can itself function as a receiving part for the application aid.

In a further embodiment not shown, the entire belt part 9 consists of a pocket-like receiving part. In this embodiment, the distance A shown in FIG. 2*a* is largely the same length as the belt part 9.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An absorbent article comprising a main body and at least one belt part with a first end secured to the main body, and a second end, wherein the belt part has a receiving part so that the belt and an application aid cooperate when guided under a user, and
   wherein the receiving part comprises a pocket that is closed at a distal edge of the second end of the belt part and having an opening which opens toward the first end when the belt part extends in a straight line to allow insertion of at least a part of the application aid.

2. The absorbent article according to claim 1, wherein the absorbent article has a first belt part and a second belt part.

3. The absorbent article according to claim 2, wherein both the first and second belt parts have a receiving part.

4. The absorbent article according to claim 1, wherein the receiving part has been formed by folding and joining together of a belt part.

5. The absorbent article according to claim 4, wherein the receiving part has been formed by the second end of the belt part having been folded over the belt part towards the first end of said belt part so that the longitudinal sides of the belt part run substantially parallel to one another.

6. The absorbent article according to claim 1, wherein the receiving part comprises a material section arranged separately on the belt part.

7. The absorbent article according to claim 6, wherein the separate material section comprises a fastening device.

8. The absorbent article according to claim 7, wherein the fastening device comprises hook or loop material.

9. The absorbent article according to claim 1, wherein the opening allows insertion of at least a part of a user's hand.

10. The absorbent article according to claim 1, wherein the pocket has a depth ranging from about 2 cm to about 20 cm.

11. An absorbent article comprising a main body and first and second belt parts, said first and second belt parts having a first end secured to the main body, and a second end, wherein the second end of at least one belt part has a receiving part,
   wherein the receiving part comprises a pocket that is closed at a distal edge of the second end of the belt part and having an opening which opens toward the first end when the belt part extends in a straight line to allow insertion of at least a part of the application aid.

12. The absorbent article according to claim 11, wherein the second ends of both the first and second belts parts have receiving parts.

13. The absorbent article according to claim 11, wherein the receiving part has been formed by the first belt part.

14. The absorbent article according to claim 13, wherein the receiving part has been formed by the second end of the belt part having been folded over the belt part towards the first end of the first belt part so that the longitudinal sides of the first belt part run substantially parallel to one another.

15. The absorbent article according to claim 11, wherein the receiving part comprises a material section arranged separately from the belt part.

16. The absorbent article according to claim 15, wherein the separate material section comprises a fastening device.

17. The absorbent article according to claim 16, wherein the fastening device comprises hook or loop material.

18. An absorbent article comprising a main body and at least one belt part with a first end secured to the main body, and a second free end, wherein the belt part has a receiving part at the second free end, and wherein the receiving part comprises a pocket, the pocket that is closed at a distal edge of the second free end of the belt part and having an opening facing the first end when the belt part extends in a straight line and at least two sides secured on the belt part.

19. The absorbent article according to claim 18, wherein the opening allows insertion of at least a part of an application aid.

20. The absorbent article according to claim 18, wherein the opening allows insertion of at least a part of a user's hand.

* * * * *